(12) United States Patent
Feller, III et al.

(10) Patent No.: US 8,167,892 B2
(45) Date of Patent: May 1, 2012

(54) ADJUSTABLE AND DETACHED STENT DEPLOYMENT DEVICE

(75) Inventors: Frederick Feller, III, Coral Springs, FL (US); Huisun Wang, Maple Grove, MN (US)

(73) Assignee: Cordis Corporation, Miami Lakes, FL (US)

( * ) Notice: Subject to any disclaimer, the term of this patent is extended or adjusted under 35 U.S.C. 154(b) by 283 days.

(21) Appl. No.: 11/321,582

(22) Filed: Dec. 29, 2005

(65) Prior Publication Data
US 2007/0156222 A1 Jul. 5, 2007

(51) Int. Cl.
*A61F 11/00* (2006.01)
*A61F 2/06* (2006.01)

(52) U.S. Cl. ........... 606/108; 623/1.11
(58) Field of Classification Search ............ 623/1.11; 606/108; 604/131, 151, 155, 164.04, 164.07, 604/165.01, 165.02, 171, 192, 198, 528; 222/391
See application file for complete search history.

(56) References Cited

U.S. PATENT DOCUMENTS

| 5,433,723 | A  | * | 7/1995  | Lindenberg et al. ........ 606/198 |
| 5,843,091 | A  | * | 12/1998 | Holsinger et al. ........... 606/108 |
| 6,024,763 | A  |   | 2/2000  | Lenker et al. |
| 6,599,296 | B1 |   | 7/2003  | Gillick et al. |
| 6,773,446 | B1 |   | 8/2004  | Dwyer et al. |
| 6,939,352 | B2 |   | 9/2005  | Buzzard et al. |
| 2002/0072712 | A1 |   | 6/2002 | Nool et al. |
| 2003/0167060 | A1 | * | 9/2003 | Buzzard et al. ............. 606/108 |
| 2004/0181239 | A1 | * | 9/2004 | Dorn et al. ................... 606/108 |

FOREIGN PATENT DOCUMENTS

| EP | 1302178 B1 | 4/2003 |
| WO | WO 00/78246 A2 | 12/2000 |
| WO | WO 2006/135551 A2 | 12/2006 |

OTHER PUBLICATIONS

European Search Report dated Apr. 14, 2009 for corresponding Patent Application No. 06 256 584.1-1257.

* cited by examiner

*Primary Examiner* — Gary Jackson
*Assistant Examiner* — Katherine Dowe

(57) ABSTRACT

The present disclosure is directed to a device for housing and retaining a delivery system for a self-expanding implant while providing means for actuating the delivery system.

1 Claim, 3 Drawing Sheets

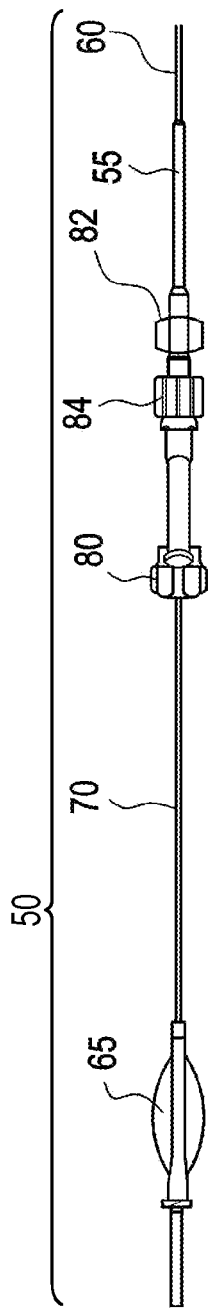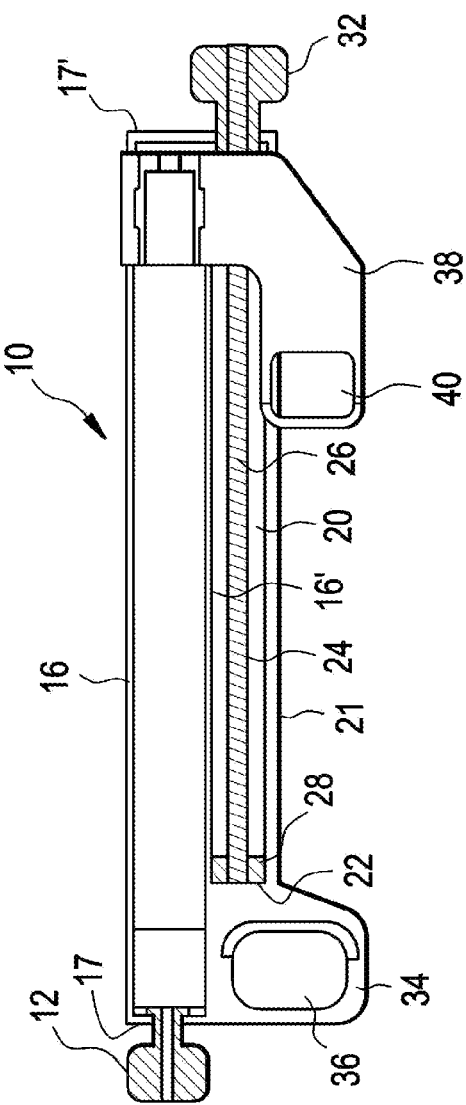

ADJUSTABLE AND DETACHED STENT DEPLOYMENT DEVICE

FIELD OF THE INVENTION

The present invention is directed to a medical device, and in particular to a tray or handle adapted to receive a delivery system for a stent or other medical device.

BACKGROUND OF THE INVENTION

Medical device delivery systems for self-expanding implants are generally advanced within a body of a patient along a desired vascular path or other body passageway, until the medical device within the catheter system is located at the treatment site. As a general matter, while watching the relative positions of the medical device and the catheter system components with respect to a stenosis on a video x-ray fluoroscopy screen, the physician holds the proximal hub attached to the inner shaft member in a fixed position with one hand, while simultaneously gently withdrawing the proximal hub attached to the outer tubular sheath with the other hand.

The deployment operation may require a measure of skill and experience. For example, among these reasons is the dynamic blood flow at the desired site for treatment, which may be further disrupted by the presence of a lesion or stenosis to be treated. Another factor is the gradual resilient expansion of a medical device as the outer sheath is retracted. This gradual expansion presents an opportunity for a "watermelon-seed" phenomenon to occur. This watermelon-seed effect may cause the resilient medical device to apply a force against the outer sheath, such that the self-expanding implant can move forward.

Thus, the physician may need to accurately hold the two proximal hubs in a desired specific arrangement and positioning, in which the hubs are properly held against the expansion force, while further attaining and maintaining accurate positioning of the medical device until it contacts the vessel. In a successful deployment and positioning of the medical device, the inner shaft of the delivery system should preferably be held stationary in the desired position. If the physician's hand that holds the inner shaft hub moves inadvertently during deployment, it is possible that the medical device may be deployed in a non-optimum position.

Also, the elongated inner and outer catheter shaft members may exhibit weakness which may present an opportunity for the position and movement of each proximal hub to differ from the position and movement of the respective distal ends of the inner and outer shaft members. Yet another factor is that the position of the medical device may be adjusted up until the point at which a portion of the expanding portion of the medical device touches the sidewalls of the body passage, so that the position of the medical device should preferably be carefully adjusted until immediately before a portion of the medical device touches the anatomy.

Some known catheter systems require two-handed operation, such as those with a pair of independent hubs, one hub on the inner and outer shaft member, respectively. Other known catheter systems include a pistol and trigger grip, with a single mode of deployment, involving a single trigger pull to deploy the associated medical device.

Accordingly, although physicians may be capable of operating such known systems with great skill, it is desirable to provide an improved catheter delivery system capable of facilitating easier and more accurate deployment and positioning of resiliently expansive medical device.

In addition, it is desirable to provide an advanced catheter deployment mechanism having two modes of operation. In the first mode of operation, the delivery mechanism preferably provides a precisely adjustable link between the inner and outer catheter shaft members, such that the relative position of the outer sheath with respect to the inner catheter shaft member can be precisely and selectively adjusted. Yet at any selected position, the delivery mechanism should preferably maintain this selected relative position of the inner and outer catheter shaft members, while resisting any force that may be present tending to move the inner or the outer catheter shaft members with respect to the other. In a second mode of operation, the delivery mechanism should preferably enable the physician to rapidly withdraw the outer tubular sheath with respect to the inner catheter shaft member preferably in a proximal direction with a single easy motion.

SUMMARY OF THE INVENTION

The present invention seeks to improve deployment accuracy of medical devices, such as self-expanding implants The present invention seeks to provide an improved system for delivery of medical devices, such as self-expanding stents, self-expanding stent-grafts, and self-expanding filters, in a system that can generally be operated with one hand.

The present invention is directed to an adjustable and detachable stent deployment device adapted to receive and operate a stent delivery system of the kind known in the art. The stent deployment device of the present invention generally includes a housing having a tray for receiving and retaining the proximal portion of a stent delivery system, and in particular, for receiving and retaining the portion of the stent delivery system that includes the controls for the device. That is, the portion of the device including the controls manipulated by the physician in deploying the medical device or stent within a patient's body. The stent deployment device further includes finger holes adapted to receive the least two fingers of the physician in operable engagement with the device. In a preferred arrangement, a first finger hold is provided in a handle portion attached to the tray in a fixed arrangement, and a second finger hole is provided in a second handle portion attached to the tray in a moveable arrangement. Also, the second, movable handle portion is provided with structure that couples to the portion of the stent delivery system that is operable during stent deployment, Thus, by moving the second handle portion of the stent deployment device, essentially by finger or hand movement, the stent deployment system can be operated by the physician in a one-handed arrangement.

In a more specific embodiment, the stent deployment device is provided with an adjustment mechanism for initial deployment of the stent delivery system. The adjustment mechanism can be an adjustment knob coupled to a lead screw which can be turned in order to deploy the device. The lead screw can be provided with a threaded arrangement or the like, which threaded arrangement couples to threads associated with the movable second handle portion. At the least, with this arrangement, it is believed that the precision of initial deployment can be improved by using the initial deployment mechanism to overcome the relatively stronger forces associated with static friction, as the sheath or the like is initially retracted from the stent.

The present invention may provide several advantages individually, or any combination of such advantages, including for example: (i) single-handed operation of the medical device delivery system; (ii) a mechanism providing leverage or mechanical advantage, to adjust or reduce the forces needed to operate the system; (iii) improved accuracy in positioning the medical device during deployment; (iv) a capability of holding the delivery system components in a fixed relative position during an intermediate point in deploying a medical device; and (v) multiple operational modes of operation, including for example a first mode of fine and precise control of the deployment process, and a second mode of rapid and easy deployment.

BRIEF DESCRIPTION OF THE DRAWINGS

FIG. 1a is a top plan view depicting a stent deployment system;

FIG. 1b is a top plan view depicting the stent deployment device of the present invention;

DETAILED DESCRIPTION OF THE INVENTION

Figure 1C:
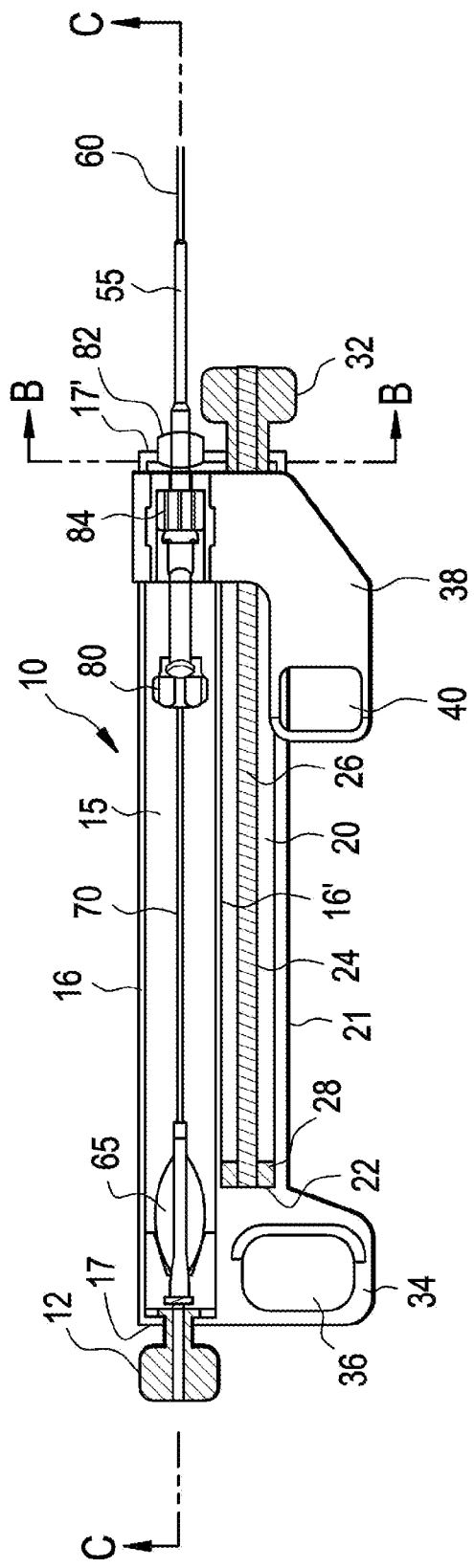
FIG. 1c is a top plan view of a stent deployment system positioned in the stent deployment device.
Figure 2:
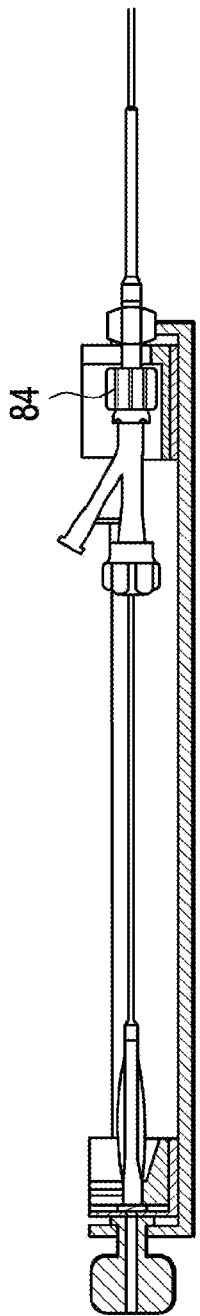
FIG. 2 is a cross sectional view of the present invention along line C-C.

As the present invention is directed to a deployment device for retaining and operating a stent delivery system, it should be noted that the above-identified figures depict a stent delivery system that is retained within the device. While the stent delivery system is not per se envisioned to comprise part of the invention, its inclusion in the description and figures facilitates the understanding of the present disclosure. In any event, it should be understood that the stent delivery systems for use in the deployment devices of the present invention may be those known in the art. For example, one such stent delivery system suitable for use in the present invention is discloses in U.S. Pat. No. 6,773,446, which is assigned to the assignee of the present application. Yet another suitable stent delivery system is disclosed in U.S. Pat. No. 6,939,352, also assigned to the assignee of the present application. The disclosures of these patents are incorporated herein by reference.

As shown in the Figures, the stent deployment device, generally depicted as 10, is adapted to receive a stent deployment system, generally depicted as 50. The stent deployment system 50 depicted here is similar to the one disclosed in U.S. Pat. No. 6,773,446.

Stent delivery system 50 comprises inner and outer coaxial tubes, wherein the inner tube is identified as inner shaft 70 and the outer tube is identified as the sheath 55. A self-expanding stent (not shown) is located within the outer sheath, wherein the stent makes frictional contact with the outer sheath and the shaft is disposed coaxially within a lumen of the stent. Stent delivery system 50 further comprises a hub 65 at its proximal end, which includes proximal terminus (not shown), which passes through an opening at the proximal end of stent delivery device 10 and is secured therein by anchoring member 12. A relatively stiff inner shaft 70 is connected to the hub 65 extends into the Tuohy Borst valve 80 and throughout the length of the outer sheath 55 and 60.

As shown in the Figures, the stent delivery device 10 retains a number of the aforedescribed components of the stent delivery system inside of tray 15, which tray is defined by sidewalls 16, 16' proximal end wall 17 and distal end wall 17'. The distal end wall 17' includes a slot 19 for receiving knob 82 on the stent delivery system 10.

The stent delivery device 10 also includes a compartment defined by side wall 16', outer wall 21, distal end wall 17', and proximal compartment wall 22. Lead screw 24, which is provided with threads 26, extends from screw bed 28 near the proximal compartment wall 22 through opening 30 in the distal end wall 17', and is attached to adjustment knob 32.

Figure 3:
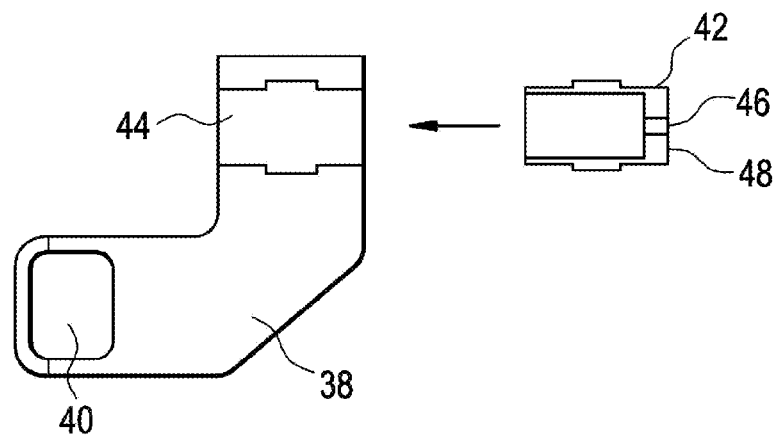
FIG. 3 is an exploded view of an aspect of the present invention.
Figure 4:
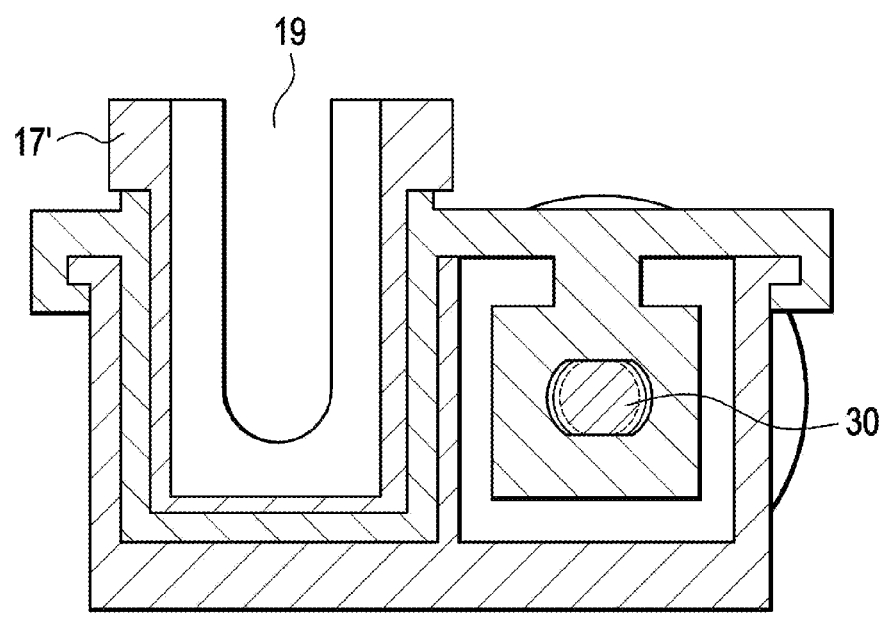
FIG. 4 is a cross sectional view of the present invention along line B-B.

The stent delivery device 10 is further provided with a first nonmovable handle 34 located at the proximal end of the device, and a second, movable handle 38 located at the distal end of the device, each of which are provided with finger holes 36 and 40, respectively. As shown in FIG. 3, the second handle 38 is provided with an insert 42 that fits within the opening 44 in the handle 38. Insert 42 is further provided with a slot 46 in distal wall 48 for receiving the proximal end of the sheath 55 of the stent delivery system. Insert 42 is provided with outer dimensions that allow it to fit in the handle opening 44, and is dimensioned on its interior to retain bearing 84 of the stent delivery system in an interference fit. Furthermore, the second movable handle can be slidably mounted on track provided on the interior of walls 16 and 16'. Also, the underside of the handle above the lead screw can be provided with threads that engage the threads of the lead screw in a complementary mating arrangement.

As can be readily appreciated by the above arrangement, the stent delivery device 10 provides a tray or housing for a stent delivery system, with the device independent of the system, that is easily assembled. The stent delivery system 50 is placed into the top opening of the device 10. The proximal terminus is secured to the device with anchoring member 12 of the device. The distal end of the system 50 is fitted within the insert 42. It should be understood that the device 10 and system 50 are disassembled with the same relative ease. Thus the device 10 is capable of being used many times, with different delivery systems.

Device 10 is constructed by techniques known in the art, such as by suitable molding operations. The device could be molded of polycarbonate, ABS, or Delrin®, an acetal resin available from DuPont, to name some suitable candidate materials. Alternatively, the device could be machined out of lightweight metals, such as titanium.

In operation, the distal end of the system 50, which comprises inner shaft 70, on which is retained a stent (not shown), which itself is retained within the lumen of the sheath 55, is inserted into the vasculature. The distal end is navigated to a target site for stent deployment. The stent is in a compressed state and makes frictional contact with the inner surface of the sheath 55.

When inserted into a patient, sheath 55 and shaft 70 are locked together at their proximal ends by, for example a Tuohy Borst valve 80, which as shown in the figures, is proximal to the insert 42. Tuohy Borst valve 80 prevents sliding movement between the shaft and sheath, which could result in a premature deployment or partial deployment of the stent. When the stent reaches its target site and is ready for deployment, the Tuohy Borst valve 80 is opened so that the sheath 55 and shaft 70 are no longer locked together.

After the valve 80 is released, the preferred operation of the present invention may be accomplished by first rotating the adjustment knob 32 to cause rotation of lead screw 24. As lead screw 24 is engaged with threads on the underside of second, movable handle 38, the turning of the lead screw causes the movable arm to move proximally on rotation of lead screw 24. This causes bearing 84, which is retained within insert 42 in interference fit, to move proximally. As bearing is engaged with the outer sheath 55 of the stent delivery system, sheath 55 retracts in the proximal direction with respect to inner shaft member 70. This first method of withdrawing the outer sheath 55, which effects a relatively fine, incremental movement of the sheath in the proximal direction, allows for precise and sensitive adjustment. The small movement sheath movement exposes a small portion of the medical device, in this case a stent, allowing the physician to hold the outer sheath 55 in position relative to the inner shaft 70, resisting further inadvertent expansion of the stent. The physician then has the time and flexibility of procedure to selectively optimize and make any final adjustments to the position of the medical device and delivery system within the desired site. This precise adjustment of the position of the stent, before any portion of the stent touches the body passage or vessel in a manner that might inhibit further positional adjustment, is preferable.

When the physician is satisfied with the positioning of the stent, as it appears on a fluoroscopic x-ray video screen, the physician may continue to rotate the adjustment knob 32 to further withdraw the outer sheath. Upon initial contact of the stent with the vessel walls, or when the stent is expanded sufficiently to independently hold its position, or at any desired point, the physician may then position his hand within the finger holes provided on the stent delivery device. By way of example the physician might place the thumb within the first, non movable handle portion and the middle finger within the second, movable handle portion. The physician can then pull the second movable handle portion in the proximal direction, providing a second way to withdraw the outer sheath. In this way, deployment occurs with relatively large-scale and rapid movement, at whatever speed the physician wishes, to quickly deploy the medical device.

It should be understood that the physician may opt for relatively quick and rapid stent deployment, and thus may forego fine operation of the adjustment knob, or may operate the adjustment knob in a relatively minimal manner, such as by using the adjustment knob merely for overcoming the static friction forces associated with initial retraction of the sheath over the stent, followed by rapid, single handed deployment by use of the handles provided on the device. It should also be understood that the physician may opt to use the conventional two-handed deployment method by quickly removing the stent delivery device, 10.

Although particular embodiments of the present invention have been shown and described, modification may be made to the device and/or method without departing from the spirit and scope of the present invention. The terms used in describing the invention are used in their descriptive sense and not as terms of limitations.

What is claimed is:

1. A medical device comprising:
a delivery device; and
an independent and non-integrated delivery system for a self-expanding implant, the delivery system comprising an outer sheath and an inner shaft, wherein
the delivery device is configured for receiving and operating the independent and non-integrated delivery system for a self expanding implant,
the delivery device having a tray, a first non-moveable handle with a finger hole attached to said tray, a receptacle defined by walls of the tray for receiving and retaining the independent and non-integrated delivery system for a self expanding implant, a second movable handle with a finger hole attached to the receptacle for engagement with a movable portion of the independent and non-integrated delivery system, the second moveable handle comprising an opening, a compartment adjacent the receptacle, the compartment housing a lead screw rotationally fixed to and extending from a screw bed in the first non-moveable handle through an opening in the second moveable handle and terminating with an adjustment knob having a through threaded hole and configured to allow the lead screw to thread through and extend from the threaded hole, whereby turning the adjustment knob translates to fine movement between the inner shaft and the outer sheath by allowing the lead screw to thread through and extend from the threaded hole, the second moveable handle also being configured for movement independent of the lead screw that translates into gross movement between the inner shaft and the outer sheath, and a removable insert fitted for housing with the opening in the second moveable handle and for securing, via an interference fit, a distal end of the delivery system, wherein the delivery device is readily detachable and independent from the non-integrated delivery system for a self expanding implant.

* * * * *